(12) United States Patent
Verin

(10) Patent No.: US 7,640,053 B2
(45) Date of Patent: Dec. 29, 2009

(54) CATHETERIZATION METHOD AND SYSTEM FOR CONTROLLING TIP DISPLACEMENT

(75) Inventor: Vitali Verin, Genève (CH)

(73) Assignee: Endosense S.A., Meyrin (CH)

( * ) Notice: Subject to any disclaimer, the term of this patent is extended or adjusted under 35 U.S.C. 154(b) by 1232 days.

(21) Appl. No.: 10/518,979

(22) PCT Filed: Jun. 26, 2002

(86) PCT No.: PCT/CH02/00349

§ 371 (c)(1),
(2), (4) Date: Dec. 21, 2004

(87) PCT Pub. No.: WO2004/002303

PCT Pub. Date: Jan. 8, 2004

(65) Prior Publication Data

US 2005/0203368 A1    Sep. 15, 2005

(51) Int. Cl.
*A61B 5/0402*    (2006.01)
(52) U.S. Cl. ..................... 600/509; 604/528; 606/108
(58) Field of Classification Search ............ None
See application file for complete search history.

(56) References Cited

U.S. PATENT DOCUMENTS 4,692,148 A * 9/1987 Kantrowitz et al. ......... 600/509
4,911,174 A * 3/1990 Pederson et al. ............ 600/508
5,078,678 A * 1/1992 Katims .................. 604/28
5,645,065 A    7/1997 Shapiro et al.
5,662,108 A    9/1997 Budd et al.
5,967,978 A   10/1999 Littmann et al.
6,246,898 B1   6/2001 Vesely et al.
6,370,412 B1   4/2002 Armoundas et al.

FOREIGN PATENT DOCUMENTS

EP    1 061 990 B1    9/2004

* cited by examiner

*Primary Examiner*—Kennedy J Schaetzle
(74) *Attorney, Agent, or Firm*—Rankin, Hill & Clark LLP

(57) ABSTRACT

The catheter is guided along a blood vessel of a patient by the bipolar electrode functioning as a mobile sensor on the catheter tip connected to the electronic unit to monitor the advance of the catheter and determine any modification of successive signals received from the bipolar electrode in order to detect any deviation of the catheter tip from the required path along the blood vessel and to deliver control signals comprising a GO signal, a STOP signal or an END signal to respectively enable, interrupt or terminate the advance of the catheter. The bipolar electrode moreover serves to verify the contact of the catheter tip with the wall of the heart cavity of the patient by creating impulses and detecting the appearance of corresponding induced signals on a surface cardiogram of the patient. The combination of the bipolar electrode on the catheter with the electronic unit provides a portable catheterization system particularly suitable for performing urgent cardiac catheterizations outside hospitals.

5 Claims, 3 Drawing Sheets

CATHETERIZATION METHOD AND SYSTEM FOR CONTROLLING TIP DISPLACEMENT

FIELD OF INVENTION

The present invention relates to a method and system for guiding a catheter along a blood vessel of a patient especially for carrying out a cardiac catheterization.

BACKGROUND OF INVENTION

Conventional catheterizations controlled by fluoroscopy are generally performed in hospitals, require complex X-ray equipment installed in a particular hospital facility such as a catheterization laboratory or radiology department and must be carried out by specially qualified physicians trained in catheterization procedures—Consequently, these conditions cannot be met in emergencies when the equipment and trained personnel required for catheterization are not readily available.

However, in many cases where there is an urgent need for catheterization, the rapid transfer of severely ill patients to a suitably equipped location can be quite problematic and may entail serious risks, even in the case of in-hospital interventions. The transfer of a patient to the next suitably equipped hospital usually takes some time and could affect the patients chances of survival.

The U.S. Pat. No. 5,391,199, U.S. Pat. No. 6,246,898 and the patent publication WO9945994 may illustrate the prior art relating to conventional catheterization using fluoroscopy imaging to show the progress of a catheter through a patient's body.

A system for externally locating a catheter described in U.S. Pat. No. 4,173,228, U.S. Pat. No. 5,425,367 and U.S. Pat. No. 5,645,065 comprises an external probe for locating a catheter tip having an inductive coil for delivering an induced signal in response to a rotating magnetic field generated by the external probe.

However, in the majority of situations requiring catheterization, the heart's structures are the main targets of interest for intervention and they constitute moving targets with variable coordinates, which can only be determined with a limited degree of accuracy.

Externally positioned 3-D sensors do not allow the intravascular position of the catheter to be ascertained and some degree of control by fluoroscopy is nevertheless necessary.

SUMMARY OF THE INVENTION

An object of the present invention is to effectively avoid the drawbacks and limitations of X-ray equipment currently required for catheterizations in hospitals by providing a compact, portable catheterization system suitable for widespread use to rapidly perform catheterizations in different settings by various types of medical personnel.

The present invention enables the advance of a catheter to be effectively monitored by using signals delivered by a mobile sensor to detect any deviation preventing the advance of the catheter.

The term catheter is generally applied here in its broadest possible sense in connection with the present invention and is meant to include any elongated flexible member such as a cardiac catheter, guide wire, pacemaker lead or the like guided along a blood vessel in accordance with this invention.

Signals delivered by the mobile sensor arranged on the catheter according to the present invention represent impulses associated with the cardiac activity and correspond to an internal cardiogram of a patient, and have thus been called cardiac signals with reference to the invention.

The present invention now makes it possible to effectively guide a catheter along a blood vessel by combining a mobile sensor with an electronic unit to enable or interrupt the advance of the catheter.

Said signals delivered by the mobile sensor are modified by an inversion of the position of the catheter tip and enable any deviation preventing the advance of the catheter to be detected.

Consequently, the catheter may provided with any suitable mobile sensor according to the invention to deliver signals that are modified by any deviation preventing the advance of the catheter so as to directly or indirectly indicate any inversion of the position of the catheter tip or a corresponding reversal of the direction of the flow of blood at the catheter tip.

A method of guiding a catheter in accordance with the invention thus provides for monitoring the advance of the catheter by detecting any inversion of the position of the catheter tip with respect to its advance along the blood vessel and returning the catheter tip to a position enabling its advance.

This method comprises generating monitoring signals related to the cardiac activity and delivered during the advance of the catheter by a mobile sensor on the catheter, comparing said monitoring signals with a reference, enabling the advance of the catheter when said signals correspond to said reference and interrupting the advance when said monitoring signals deviate from said reference.

A bipolar electrode may advantageously used to obtain monitoring signals corresponding to a reference voltage to enable the advance of the catheter or to a second voltage to interrupt its advance.

A method of catheterization according to the invention comprises: generating monitoring signals related to the cardiac activity and delivered during the advance of the catheter by at least one mobile sensor on the catheter adapted to deliver cardiac signals corresponding to impulses associated with the cardiac activity and representing an internal cardiogram of a patient undergoing catheterization; enabling the advance of the catheter when said monitoring signals correspond to a reference; and interrupting the advance when said monitoring signals deviate from said reference.

This method of catheterization moreover enables the position of the catheter tip in contact with the wall of the heart cavity to be verified by creating impulses at the tip of the catheter and detecting the appearance of corresponding induced signals on a surface cardiogram of the patient.

It moreover enables the entry of the catheter tip into the heart atrium of the patient to be ready verified by detecting a significant increase in the amplitude of cardiac signals corresponding to atrial impulses and appearing on said internal cardiogram.

In addition, the passage of the catheter tip from the atrium to the ventricle of the patient may be readily verified by detecting a significant increase in the amplitude of the cardiac signals corresponding to ventricular impulses and appearing on said internal cardiogram.

The present invention provides a catheterization system comprising a catheter provided with at least one mobile sensor and an electronic unit including a central processor connected to said mobile sensor via a filter, an analog-to-digital converter and a signal processor and adapted to compare said cardiac signals and to deliver a GO signal a STOP signal and an END signal to respectively enable, interrupt or terminate the advance of the catheter.

The catheterization system may moreover advantageously comprise a device for obtaining a surface cardiogram, said device being connected to said central processor via a second filter, a second analog-to-digital converter and a second signal processor.

Said catheterization system may be advantageously provided with a mobile sensor comprising a bipolar electrode adapted to deliver said cardiac signals and to generate impulses.

The invention may be advantageously carried out to meet various diagnostic and therapeutic functions by means of such a catheterization system wherein the catheter is provided with one or more types of mobile sensors selected from the group including a bipolar electrode, a flow sensor, a pressure sensor, a deflection sensor and an ultrasonic sensor.

The invention may be illustrated by the embodiment described below by way of example with reference to the accompanying drawings.

DESCRIPTION OF PREFERRED EMBODIMENTS

Figure 1:
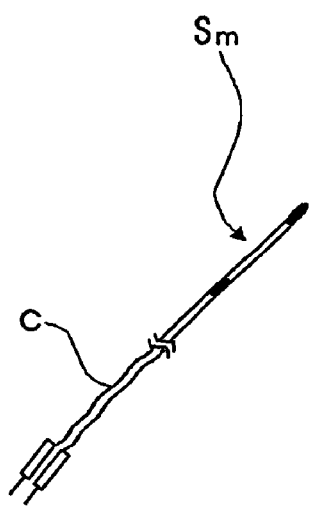
FIG. 1 shows a bipolar electrode on the free end of a catheter.

The tip of the catheter C shown in FIG. 1 is provided with a mobile sensor Sm in the form of a bipolar electrode serving to deliver cardiac signals cs representing electrical impulses associated with the cardiac activity and including a ventricular signal cv and an atrial signal ca corresponding respectively to the ventricular complex and to the atrial wave of an internal cardiogram of a patient undergoing catheterization. The bipolar electrode Sm also enables the emission of electrical impulses in the heart of the patient.

Figure 2A:
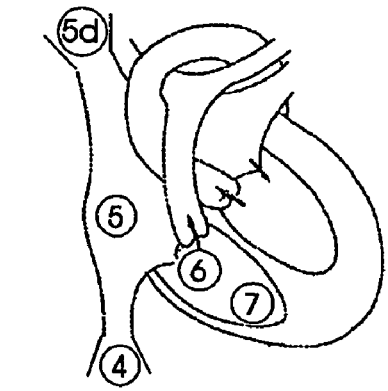
FIG. 2a is a schematic view of the heart region of the patient undergoing a cardiac catheterization FIG. 2b to 2d indicate possible deviations of the catheter tip from the catheterization path.
Figure 2:
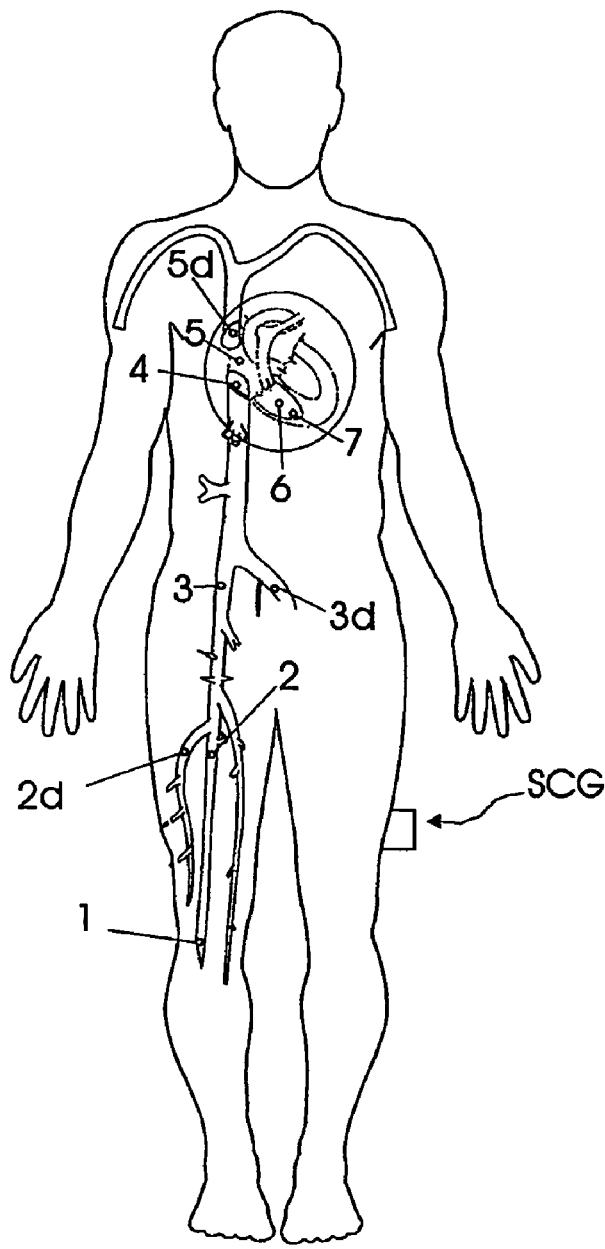
FIG. 2 illustrates the path of the catheter in a patient undergoing a cardiac catheterization.

FIG. 2 represents points 1 to 4 indicating various positions of the bipolar electrode Sm on the path of the catheter C extending from the femoral vein to the vena cava inferior of a patient and points 5 and 6, 7 respectively indicating positions of the catheter tip in the right atrium and in the right ventricle of the patient's heart. FIGS. 2 and 2a further represent the points 2d, 3d and 5d indicating possible deviations of the catheter tip from the required path 1 to 7.

A device SCG for measuring a surface-cardiogram, comprising stationary sensors in contact with the skin of the patent undergoing catheterization, is further indicated schematically in FIG. 2 and serves to deliver sure cardiac signals sc including a surface ventricular signal sv and a surface atrial signal sa corresponding to the QRS-complex and the P-wave of a surface cardiogram.

FIG. 2a further shows an enlarged view of the heart region indicating the path of the catheter tip from the point 4 in the vena cava inferior to the point 5 in the right atrium and the point 6 in the right ventricle of the patient's heart. A possible upward deviation of the catheter tip from the point 5 in the right atrium to the point 5d in the vena cava superior is also indicated in FIG. 2.

Figure 2B:
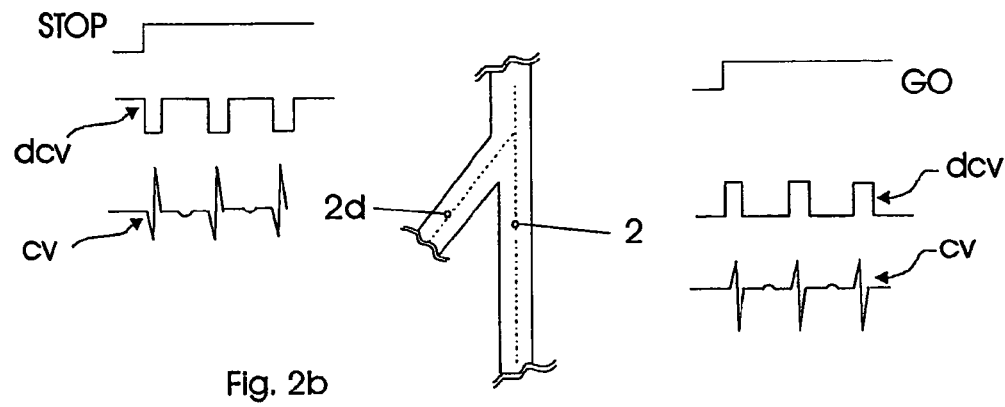

FIG. 2b schematically represents the form and polarity of the ventricular signal cv delivered by the bipolar electrode Sm and the corresponding digital signal dcv in case the catheter tip is deviated laterally as indicated in FIGS. 2 and 2a from the point 2 to the point 2d in a secondary vein. The form of the ventricular signal cv is represented schematically in FIG. 2b by the ventricular-complex and a corresponding digital signal dcv represents the polarity and the peak-to-peak amplitude of the ventricular complex.

A comparison of the points 2 and 2d shows that the signal cv delivered after the lateral deviation to the point 2d is inverted with respect to that delivered at the previous point 2, the signal cv at the point 2d having a descending branch before an ascending branch of the ventricular complex, the corresponding digital signal dcv being negative at the point 2d, as opposed to the positive digital signal dcv at the point 2, at which the signal cv has the usual form of a ventricular signal complex comprising an ascending branch followed by a descending branch.

Figure 2C:
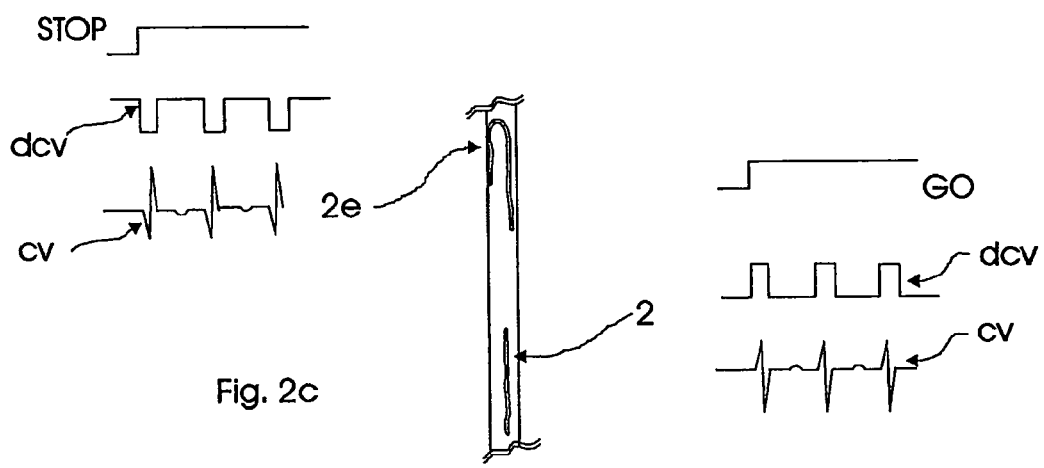

FIG. 2c similarly illustrates the form and polarity of the ventricular signal cv delivered by the bipolar electrode Sm in case the catheter tip is deviated downwards and folded to the inverted position indicated at the point 2e.

A comparison of the points 2 and 2e shows that the signal cv delivered at the point 26 is invert with respect to that delivered at the previous point 2, the signal cv at the point 2e having a descending branch before an ascending branch, the corresponding digital signal dcv being negative at the point 2e, as opposed to the signal dcv at the point 2, at which the signal cv has the usual form of a ventricular signal comprising an ascending branch followed by a descending branch.

Figure 2D:
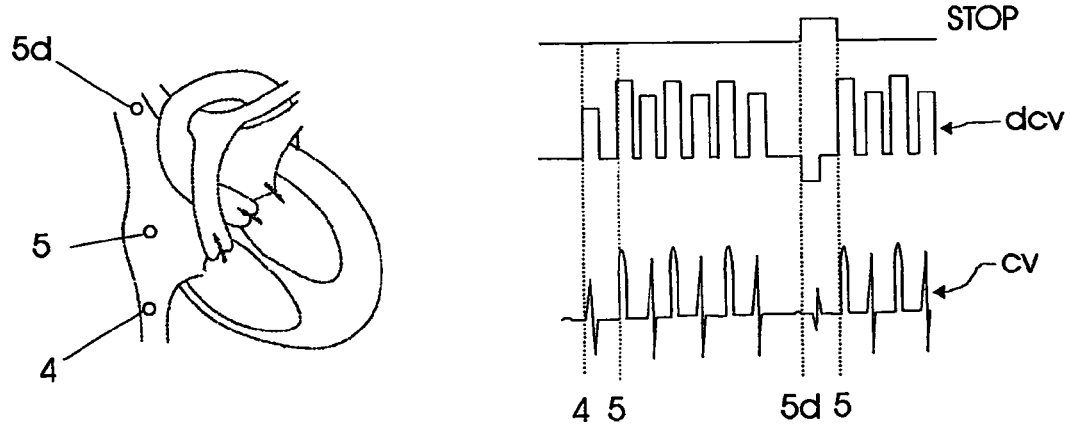

FIG. 2d moreover illustrates the form and the polarity of the ventricular signal cv delivered by the bipolar electrode Sm in case the catheter tip is deviated upwards from the point 5 in the right atrium of the heart to the point 5d in the vena cava superior.

A comparison of the points 5 and 5d shows that the signal cv delivered at the point 5d is inverted with respect to that delivered at the previous point 5, the ventricular signal cv at the point 5d having a descending branch before an ascending branch, the corresponding signal dcv being negative at the point 5d, as opposed to the positive signal dcv at the point 5, at which the signal cv has the usual form of a ventricular signal comprising an ascending branch followed by a descending branch.

It may moreover be seen from FIG. 2d that significant analog and digital atrial signals ca and dca appear between the analog and digital ventricular signals cv at the point 5 situated in the right atrium of the patient's heart.

Figure 3:
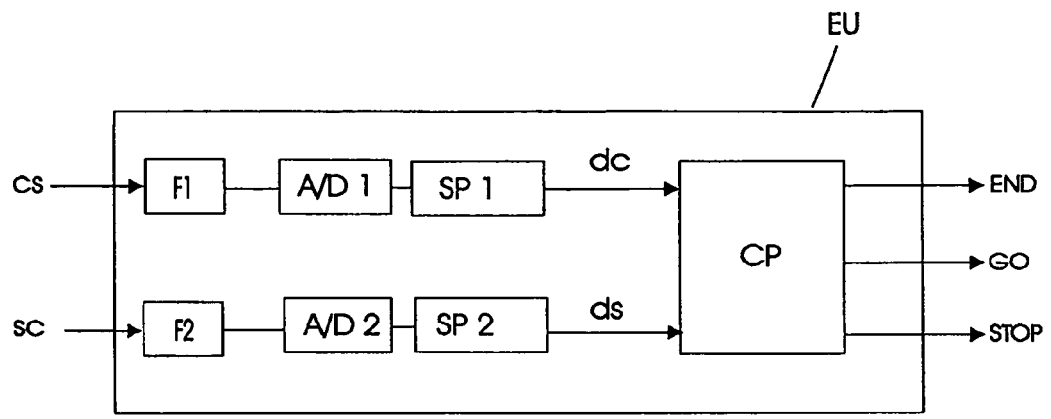
FIG. 3 represents a block diagram of an electronic unit associated with the bipolar electrode.

The electronic unit EU represented in FIG. 3 comprises a central processor CP which is connected to the bipolar electrode Sm (FIG. 1) via a filter F1, an analog-to-digital converter A/D1 and a signal processors SP1 and is further connected to the surface-cardiogram device SCG via a second filter F2, a second analog-to-digital converter A/D2 and a signal processor SP2.

The signal processor SP1 serves to deliver digital cardiac signals dc corresponding to the polarity and the amplitude of the successive internal cardiac signals cs received from the bipolar electrode Sm during the advance of the catheter C.

The second signal processor SP2 serves to deliver digital time signals ds corresponding to the ventricular component sv of the successive surface cardiac signals sc received from the surface-electrocardiogram device SCG (FIG. 2).

The central processor CP is arranged to compare the polarity and the peak-to-peak amplitudes of the ventricular complex of successive signals cv received from the bipolar electrode Sm via the filter F1, the converter A/D1 and the signal processor SP1 and to deliver three control signals comprising: a GO signal serving to enable the advance of the catheter C when the signal cv is positive and its peak-to-peak amplitude increases during the advance of the catheter, a STOP signal serving to interrupt the advance of the catheter when said signal cv becomes negative and its amplitude decreases and an END signal serving to terminate the advance of the catheter when it has reached its target in the heart.

Figure 4:
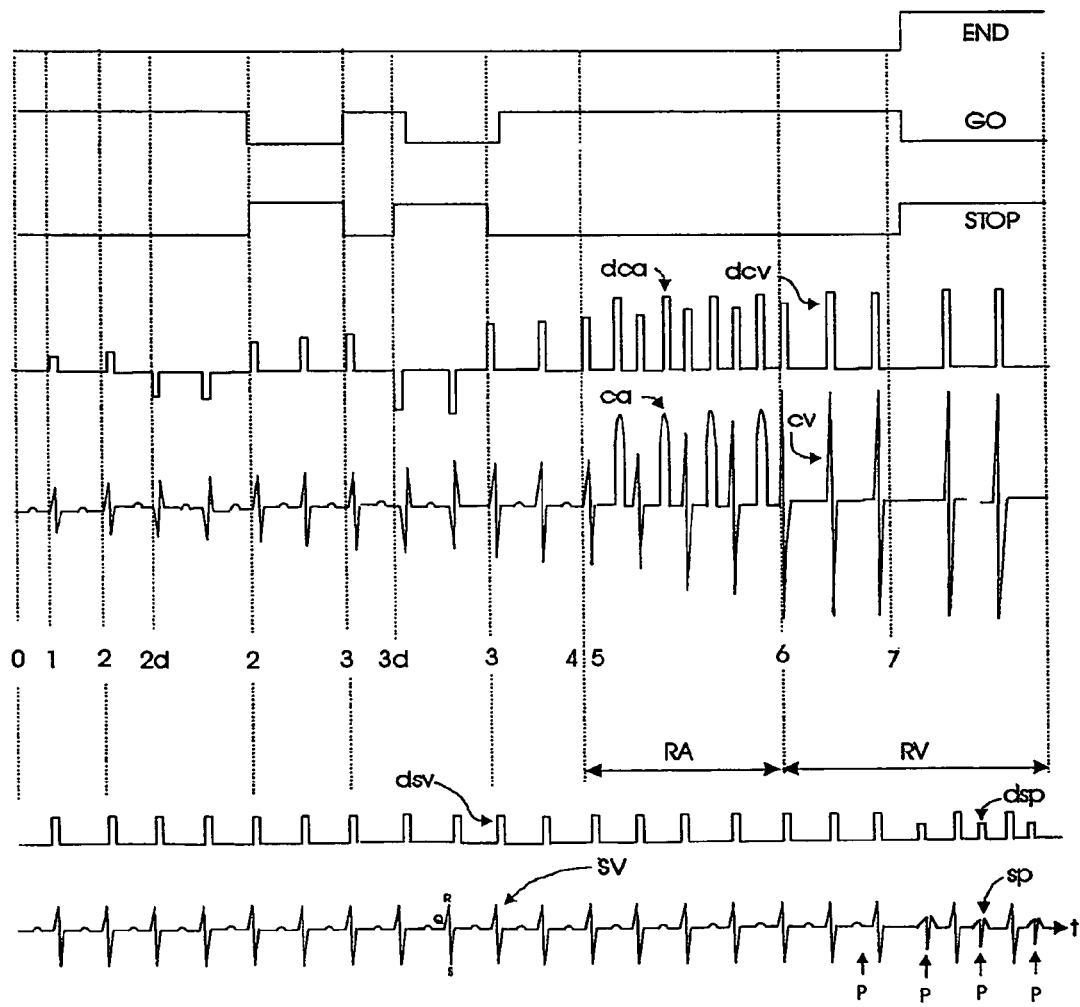
FIG. 4 illustrates various signals relating to the catheterization.

FIG. 4 illustrates the variation of the successive digital signals de obtained from the bipolar electrode Sm on the catheter tip, as well as the modification of the control signals GO, STOP, END obtained from the electronic unit EU, as a function of time t, during the cardiac catheterization along the path indicated by the points 1 to 7 in FIG. 2.

It may be seen from FIG. 4 that the digital ventricular signal dc obtained from the bipolar electrode Sm and the control signal GO from the electronic unit EU remain positive as long as the bipolar electrode is situated at the points 1 to 6 along the catheterization path indicated in FIG. 2.

As may further be seen from FIG. 4, the amplitude of the analog and digital ventricular signals cv, dcv increases gradually as the catheter tip advances along the path from the point 1 to the point 7.

On the other hand, as soon as the catheter tip is deviated to the points 2d or 3d, the digital signal cd becomes negative and the control signal GO becomes negative and the STOP signal become positive in order to interrupt the advance and enable the deviation to be corrected by partially withdrawing and rotating the catheter and so as to return it respectively from the point 2d to the point 2 and from the point 3d to the point 3.

FIG. 4 further shows that, when the catheter tip passes from the point 4 in the vena cava inferior to the point 5 in the right atrium RA of the patient's heart, the digital sigal dc obtained from the bipolar electrode Sm exhibits a sudden increase of the analog and digital atrial signals ca and dca, which clearly appear between the ventricular signals cv and dcv, so that the presence of the catheter tip can be thereby definitely established within the right atrium RA of the patient.

It can also be seen from FIG. 4 that said atrial signals ca and dca disappear once more as soon as the catheter tip passes at the point 6 from the right atrium RA into the right ventricle RV, so that the presence of the catheter tip can be thereby also clearly established within the right ventricle RV of the patient.

It may be noted that the final point 7 corresponds in this case to the target of the cardiac catheterization where the catheter tip lies in contact with the wall of the right ventricle RV of the patient's heart and the electronic unit delivers an END signal to terminate the advance of the catheter.

The analog and digital ventricular signals sv and dsv obtained from the device SCG are finally shown in FIG. 4 and correspond to a surface cardiogram of the patient undergoing catheterization.

The contact of the catheter tip with the wall of the right ventricle RV may be verified by creating periodic pulses on the ventricle wall and detecting the appearance of corresponding induced signals sp and dsp between the successive ventricular signals sv and dsv in the surface cardiogram obtained by means of the device SCG. The vertical arrows marked P at the bottom of FIG. 4 indicate each time a periodic pulse is applied to the wall of the right ventricle RV. Said periodic pulses may be obtained by periodic tapping of the catheter tip on the wall of the right ventricle, or by generating periodic electric impulses from the bipolar electrode Sm on the catheter tip in contact with the wall of the right ventricle.

The described combination of the bipolar electrode Sm on the catheter tip with the device SCG and the electronic unit EU thus enables the electronic unit to detect the induced signal dsp, to deliver an END signal and to control the contact of the bipolar electrode with the wall of the right ventricle.

The present invention provides a combination of advantages which effectively overcome the drawbacks and limitations of conventional catheterization under the control of fluoroscopy as well as alternative techniques proposed to control the insertion of catheters by 3-D imaging or external catheter-tip detectors. The following advantages of the invention may be cited by way of exile.

a. Catheterization can be performed without requiring fluoroscopy.

b. As opposed to entirely manual control of catheterization using 3-D imaging or external catheter tip detectors systems, the present invention achieves a major progress due in view of the fact that information associated with the cardiac cycle is now obtained from the movable and stationary sensors respectively on the catheter tip and on a patient's skin and processed by the electronic unit so as to automatically deliver control signals which enable or halt the progress of the catheter.

c. Catheterization can now be achieved with very compact equipment which can be easily transported and applied as required in various settings such as an ambulance, a patient's home, a public place or a physician's practice, as well as in various hospital locations not usually equipped with fluoroscopy such as an Intensive Care Department, an Operating Room or the like.

d. The use of the catheter-guiding system according to the invention is highly simplified thanks to control signals delivered by the electronic unit can be readily used by various types of medical personnel trained in vessel puncture, such as ambulance physicians, anesthesiologists, nurses or paramedics.

e. Consequently, catheterizations may now be duly achieved in emergencies for various purposes such as establishing a diagnosis (endocavitary ECG in arrhythmia), monitoring (pulmonary artery pressure monitoring) and delivering a corresponding therapeutic intervention (endocavitary pacing, arrhythmia overdrive, defibrillation, clearing arterial obstructions).

f. The heart structures constituting moving targets with unknown coordinates may be reached by combining the mobile and stationary sensors on the catheter tip and on the patient's skin with the electronic unit in accordance with the invention.

g. Transmission of the internal cardiograms is interrupted in case the tip of the catheter perforates the blood vessel, so that the advance of the catheter may be interrupted via the electronic unit in order to enable the return of catheter to the blood vessel, thereby increasing the security of the on procedure.

h. The combination of the catheter with the electronic unit may be readily adapted to meet most diagnostic, therapeutic and monitoring functions that may be required when performing catheterization procedures for different purposes.

The above advantages may moreover be achieved by different variants of the catheterization system described above by way of example.

The invention may be carried out with various types of sensors such as pressure sensors or acoustic sensors provided on the catheter tip in addition to or instead of a bipolar electrode.

The catheter may be provided for example with various combinations of a bipolar electrode with a pressure sensor, a flow sensor adapted to determine the direction and speed of the blood flow, or an acoustic sensor, notably an ultrasound sensor. Such combinations of sensors may moreover be adapted to provide various types of information of interest regarding the cardiac activity, the blood circulation and the blood vessel of a patient.

The invention is particularly suitable for applications requiring cardiac catheterizations to be performed in case of emergency when special hospital facilities and personnel are not readily available.

The invention claimed is:

1. A method of cardiac catheterization for controlling displacement of a catheter tip with respect to a heart of a patient and correcting any undesirable deviation of the catheter tip, comprising the steps of:
   (a) producing monitoring signals during advancement of the catheter along a blood vessel by providing the catheter (C) with at least one sensor (Sm) adapted to deliver cardiac signals that represent an internal cardiogram of the patient and are modified by any deviation of the catheter tip preventing the advance of the catheter,
   (b) comparing said monitoring signals with a reference during the advance of the catheter,
   (c) enabling the advance of the catheter when said monitoring signals correspond to said reference and interrupting the advance of the catheter when said monitoring signals deviate from said reference in order to return the catheter tip to a position enabling its advance.

2. The method according to claim 1, comprising the further step of verifying entry of the catheter tip into a heart atrium of the patient by detecting an increase in amplitude of cardiac signals corresponding to atrial impulses appearing on said internal cardiogram of the patient.

3. The method according to claim 2, comprising the further step of verifying passage of the catheter tip from the atrium to a ventricle of the patient by detecting a significant increase in the amplitude of the cardiac signals corresponding to ventricular impulses that appear on said internal cardiogram of the patient.

4. The method according to claim 3, comprising the further step of verifying contact of the catheter tip with a wall of the heart cavity by creating impulses at the tip of the catheter and detecting the appearance of corresponding induced signals on a surface cardiogram of the patient.

5. A cardiac catheterization system, comprising:
   (a) a catheter (C) provided with at least one sensor (Sm) that comprises a bipolar electrode and a flow sensor and is adapted to deliver cardiac signals that represent an internal cardiogram of a patient undergoing catheterization and are modified by any deviation of the catheter tip preventing advance of the catheter,
   (b) a central processor (CP) connected to said sensor (Sm) via a first filter (FI), a first analog-to-digital converter (A/D 1) and a first signal processor (SP1), said central processor (CP) further being connected to a device (SCG) for obtaining a surface cardiogram of the patient via a second filter (F2), a second analog-to-digital converter (A/D2) and a second signal processor (SP2), said central processor (CP) being adapted to deliver a GO signal, a STOP signal and an END signal to respectively enable, interrupt or terminate the advance of the catheter.

* * * * *